United States Patent [19]

Grabowski et al.

[11] Patent Number: 4,894,450

[45] Date of Patent: Jan. 16, 1990

[54] PROCESS FOR 2-(AMINOALKYLTHIO) CARBAPENEMS

[75] Inventors: Edward J. J. Grabowski, Westfield; David L. Hughes, Old Bridge, both of N.J.

[73] Assignee: Merck & Co., Inc., Rahway, N.J.

[21] Appl. No.: 48,341

[22] Filed: May 11, 1987

[51] Int. Cl.$^4$ .............................. C07D 487/04
[52] U.S. Cl. ....................................... 540/350
[58] Field of Search ........................... 540/350

[56] References Cited

U.S. PATENT DOCUMENTS

| | | | |
|---|---|---|---|
| 4,290,947 | 9/1981 | Christensen | 260/239 A |
| 4,292,436 | 9/1981 | Liu | 560/148 |
| 4,329,481 | 5/1982 | Liu | 556/410 |
| 4,378,315 | 3/1983 | Christensen | 260/239 A |
| 4,536,335 | 8/1985 | Kim | 260/245.2 T |
| 4,552,696 | 11/1985 | Kim | 260/245.2 T |
| 4,640,799 | 2/1987 | Kim | 540/350 |

OTHER PUBLICATIONS

March, Advanced Organic Chemistry, pp. 296–297, (1985).

Flockerzi, Helv Chim Acta, 66, 2069, (1983) Abstract only.

M. Sletzinger et al., "A Facile Transformation of Bicyclic Keto Esters to Bisprotected ($\pm$)-8-Epithienamycin via Enol Activation", Tetrahedron Lett., 21, 4221–4224, (1980).

D. G. Melillo et al., "A Practical Synthesis of ($\pm$)-Thienamycin", Tetrahedron Lett., 21, 2783–2786, (1980).

I. Shinkai et al., "A Direct Transformation of Bicyclic Keto Esters to N–Formimidoyl Thienamycin", Tetrahedron Lett., 23, 4903–4906, (1982).

*Primary Examiner*—Robert Gerstl
*Attorney, Agent, or Firm*—Raymond M. Speer; Hesna J. Pfeiffer

[57] ABSTRACT

This invention relates to a process for preparing 2-(aminoalkylthio)carbapenems. In particular, this invention relates to a process in which a bis(substituted phenyl) phosphorohalidate is used to form an enol phosphate intermediate that can be converted to 2-(aminoalkylthio)carbapenems by reaction with suitable thioalkylamines.

3 Claims, No Drawings

PROCESS FOR 2-(AMINOALKYLTHIO) CARBAPENEMS

BACKGROUND OF THE INVENTION (a) Field of the Invention

This invention relates to a process for preparing 2-(aminoalkylthio)carbapenems. In particular, this invention relates to a process in which a bis(substituted phenyl) phosphorohalidate is used to form an enol phosphate intermediate that can be converted to 2-(aminoalkylthio)carbapenems by reaction with suitable thioalkylamines.

Certain of the 2-(aminoalkylthio)carbapenems prepared by the process of this invention are themselves esters of useful antibiotics, such as thienamycin. The 2-(aminoalkylthio)carbapenems prepared by the process of this invention may also be used as intermediates in the preparation of other useful carbapenem antibiotics, such as N-formamidoyl-thienamycin.

(b) Prior Art

Sletzinger et al., *Tetrahedron Lett.*, 21, 4221–4224 (1980), have reported a procedure for converting a ketone carboxylate ester of Formula A

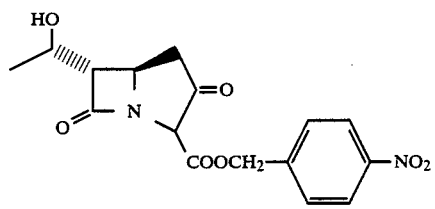

to an enol phosphate intermediate of Formula B

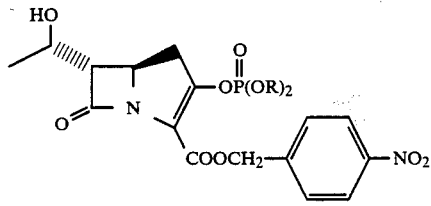

wherein R is ethyl or phenyl, and subsequently to a corresponding 8-epithienamycin derivative of Formula C.

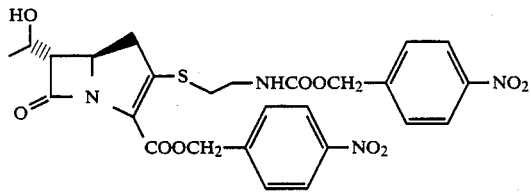

The process of the present invention uses various bis(-chloro-substituted phenyl) phosphorochloridates to achieve surprisingly improved yields of n-formamidoyl-thienamycin relative to the corresponding unsubstituted diphenyl phosphorochloridate. See Table I, Example 5, below.

SUMMARY OF THE INVENTION

Applicants have discovered an advantageous process for preparing 2-(aminoalkylthio)carbapenems of Formula I.

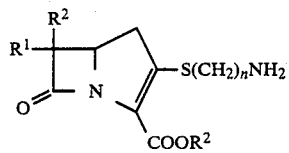

or a pharmaceutically acceptable acid addition salt thereof;
wherein $R^1$ and $R^2$ are independently:
(a) hydrogen;
(b) $C_1$–$C_4$ alkyl;
(c) $C_1$–$C_4$ alkyl substituted at the 1-position with a substituent selected from the group consisting of:
(i) hydroxy;
(ii) tris($C_1$–$C_4$ alkyl)silyloxy; or
(iii) allyloxycarbonyloxy; or
(d) fluorinated $C_1$–$C_4$ alkyl; with the proviso that at least one of $R^1$ and $R^2$ is hydrogen;
$R^3$ is:
(a) $C_1$–$C_4$ alkyl; or
(b) benzyl or benzyl substituted in the benzene ring with one to three substituents selected from the group consisting of:
(i) $NO_2$;
(ii) halogen; or
(iii) $C_1$–$C_4$ alkyl; and n is an integer of from 2 to 6.

In particular, applicants have discovered a novel process in which a bis(substituted phenyl) phosphorohalidate is used to form an enol phosphate intermediate that can be converted to a compound of Formula I by reaction with a suitable thioalkylamine. More specifically, applicants have discovered a process for preparing compounds of Formula I comprising:

(a) reacting a mixture of a tertiary amine or a hindered secondary amine and a compound of Formula II

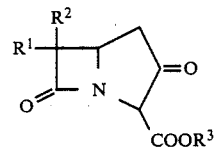

wherein $R^1$, $R^2$, and $R^3$ are defined as above; with a phosphorohalidate of Formula III

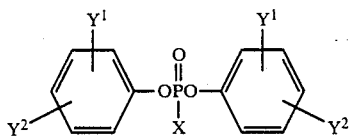

wherein $Y^1$ is halogen, $Y^2$ is hydrogen or halogen, and X is chlorine or bromine; in a substantially inert organic solvent at a temperature of from about $-80°$ to about $-40°$ to form an enol phosphate intermediate of Formula IV

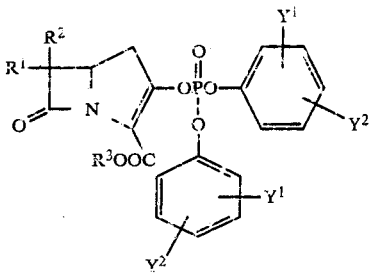

wherein $R^1$, $R^2$, $R^3$, $Y^1$, and $Y^2$ are defined as above; and (b) adding to the enol phosphate intermediate a thioalkylamine of the formula $HS(CH_2)_nNH_2$, wherein n is an integer of from 2 to 6, or a pharmaceutically acceptable acid addition salt thereof, at a temperature of from about $-90°$ to about $-40°$.

Although the structure shown for Formula II indicates one tautomeric form, it is understood that this representation is for convenience only and that the scope of this invention includes as equivalents all tautomeric forms of the compounds II used in the process of this invention.

The term "$C_1$–$C_4$ alkyl" refers to straight or branched chain aliphatic hydrocarbon groups having from 1 to 4 carbon atoms, also referred to as lower alkyl. Examples of $C_1$–$C_4$ alkyl are methyl, ethyl, propyl, butyl, and the isomeric forms thereof.

Substitution at the 1-position of $C_1$–$C_4$ alkyl refers to $C_1$–$C_4$ alkyl bearing a substituent on the carbon atom most proximately attached to the $\beta$-lactam function. For example, 1-hydroxy substituted $C_1$–$C_4$ alkyl includes hydroxymethyl, 1-hydroxy-ethyl, 1-hydroxypropyl, 1-hydroxybutyl, 1-hydroxy-2-methylpropyl, and their optical isomer forms. Similar substitution is possible for tris($C_1$–$C_4$ alkyl)silyloxy and allyloxycarbonyloxy groups. For example, 1-tris($C_1$–$C_4$ alkyl)silyloxy-substituted $C_1$–$C_4$ alkyl includes (trimethylsilyloxy)methyl, 1-(trimethylsilyloxy)ethyl, (t-butyldimethylsilyloxy)methyl, 1-(t-butyldimethylsilyloxy)ethyl, and the like.

The term "$C_1$–$C_4$ fluorinated alkyl" refers to $C_1$–$C_4$ alkyl in which one or more hydrogen atoms are replaced with fluorine atoms. Examples of $C_1$–$C_4$ fluorinated alkyl are fluoromethyl, difluoromethyl, trifluoromethyl, 1- or 2-fluoroethyl, 1,1-difluoroethyl, 2,2,2-trifluoroethyl, perfluoroethyl; other similarly mono-fluorinated, polyfluorinated, and perfluorinated ethyl, propyl, and butyl groups; and the isomeric forms thereof.

Examples of halogen are fluorine, chlorine, bromine, and iodine.

The term "pharmaceutically acceptable acid addition salt" refers to a salt prepared by contacting a compound of Formula I with an inorganic or organic acid whose anion is generally considered suitable for human consumption. Examples of pharmaceutically acceptable acid addition salts include the acetate, adipate, alginate, aspartate, benzoate, benzene-sulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, heptanoate, hexanoate, hydrochloride, hydrobromide, hydroiodide, 2-hydroxyethanesulfonate, lactate, malate, maleate, methanesulfonate, 2-naphthalene-sulfonate, nicotinate, pamoate, pectinate, 3-phenylpropionate, phosphate, picrate, pivalate, propionate, succinate, sulfate, tartrate, thiocyanate, tosylate, and undecanoate salts.

The term "substantially inert organic solvent" refers to non-protic organic liquids in which reactants may be dissolved or suspended but which are otherwise essentially chemically inert. Examples of substantially inert organic solvents include alkanes and cycloalkanes; ethers and cyclic ethers, such as diethyl ether, tetrahydrofuran, tetrahydropyran, and the like; aromatic hydrocarbons, such as toluene, xylene, and the like; halocarbons, such as chloroform, dichloromethane, ethylene dichloride, and the like; N,N-disubstituted amides, such as dimethylformamide, dimethylacetamide, and the like; N-substituted lactams, such as N-methylpyrrolidinone, N-ethylpyrrolidinone, N-methylpiperidinone, and the like; cyanoalkanes, such as acetonitrile, proprionitrile, and the like; and other such organic solvents known in the art.

DESCRIPTION OF THE INVENTION

The process of this invention may be effectuated by the general procedures illustrated in the following Schemes. Unless otherwise specified, the various substituents are defined as for Formula I above. Scheme A illustrates the general method of the process of this invention for preparing 2-(aminoalkylthio)carbapenems of Formula I.

SCHEME A

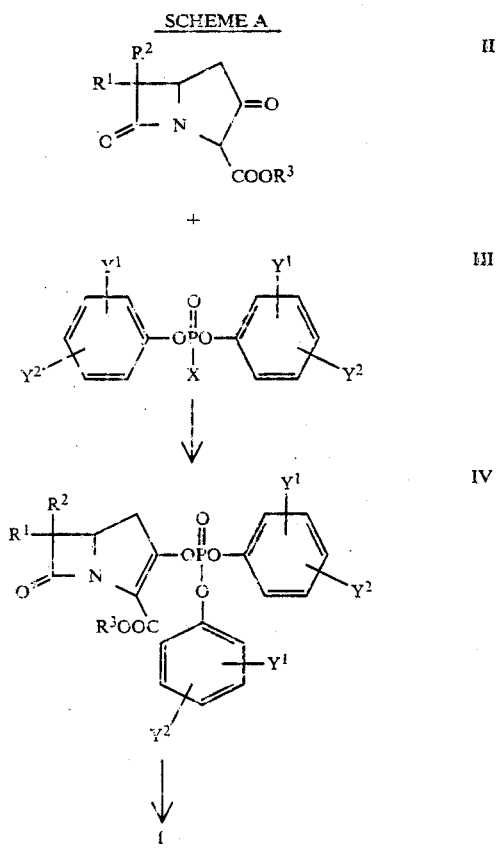

Ketone precursors of Formula II may be prepared using methods known in the art. For the preparation of the representative compound p-nitrobenzyl (3R,5R,6S)-2-oxo-6-[(1R)-1-hydroxyethyl]carbapenem-3-carboxylate (that is, Formula I in which $R^1$ is 1-hydroxyethyl in the R stereoconfiguration, $R^2$ is hydrogen, and $R^3$ is p-nitrobenzyl), see, for example, D. G. Melillo et al., *Tetrahedron Lett.*, 21, 2783–2786 (1980), and U.S. Pat. Nos. 4,378,315 and 4,290,947. Compounds of Formula II are converted to enol phosphate intermediates of Formula IV by phosphorylation with phosphorohalidates of Formula III in a substantially inert organic solvent containing a suitable tertiary amine or a hindered about −80° C. to about −40° C. Suitable tertiary amines or hindered secondary amines are organic amines that are sufficiently basic to prevent the reaction medium from becoming acidic but which do not themselves form significant quantities of byproducts by chemical reaction with other reagents or with reaction products. Suitable tertiary amines include trialkylamines, such as triethylamine, tributylamine, and diisopropylethylamine; N-substituted saturated heterocyclic compounds, such as N-methylmorpholine, N-methylpiperidine, and N,N-dimethylpiperazine; polybasic tertiary amines, such as N,N,N,N-tertramethylethylenediamine and N,N,N,N-tetramethylpropylenediamine; and other tertiary amines known in the art. Suitable hindered secondary amines include 2,2,6,6-tetramethylpiperidine and other hindered secondary amines known in the art. Preferred amines are tertiary amines, preferably diisopropylethylamine. Optimal yields of some of the enol phosphate intermediate may require the amine to be added to the reaction medium before the phosphorohalidate is added.

Substantially inert organic solvents are non-protic organic liquids in which reactants may be dissolved or suspended but which are otherwise essentially chemically inert. Examples of substantially inert organic solvents include alkanes and cycloalkanes; ethers and cyclic ethers, such as diethyl ether, tetrahydrofuran, and tetrahydropyran; aromatic hydrocarbons, such as toluene and xylene; halocarbons, such as chloroform, dichloromethane, and ethylene dichloride; N,N-disubstituted amides, such as dimethylformamide and dimethylacetamide; N-substituted lactams, such as N-methylpyrrolidinone, N-ethylpyrrolidinone, and N-methylpiperidinone; cyanoalkanes, such as acetonitrile and proprionitrile; and other such organic solvents known in the art. Preferred solvents are N-substituted lactams, preferably N-ethylpyrrolidinone.

The enol phosphate intermediates of Formula IV need not be isolated but are preferably used in situ without further isolation or purification. Enol phosphate intermediates of Formula IV (dissolved in the reaction medium, as described above) are converted to 2-(aminoalkylthio)carbapenems of Formula I by reaction with a thioalkylamine of the formula $HS(CH_2)_nNH_2$ (wherein n is an integer of from 2 to 6), or suitable pharmaceutically acceptable acid addition salt thereof, at a temperature of from about −90° C. to about −40° C. The thioalkylamine may be added as the free amine or as an acid addition salt, the selection typically being made as a matter of commercial availability or of convenience in handling rather than as a critical limitation on the process. For example, an acid addition salt may be a solid rather than a liquid. Examples of suitable pharmaceutically acceptable acid addition salts include the acetate, adipate, alginate, aspartate, benzoate, benzenesulfonate, bisulfate, butyrate, citrate, camphorate, camphorsulfonate, cyclopentane-propionate, digluconate, dodecylsulfate, ethanesulfonate, fumarate, glucoheptanoate, glycerophosphate, heptanoate, hexanoate, hydrochloride, hydrobromide, hydroiodide, 2-hydroxyethanesulfonate, lactate, malate, maleate, methanesulfonate, 2-naphthalene-sulfonate, nicotinate, pamoate, pectinate, 3-phenylpropionate, phosphate, picrate, pivalate, propionate, succinate, sulfate, tartrate, thiocyanate, tosylate, and undecanoate salts.

The 2-(aminoalkylthio)carbapenems of Formula I need not be isolated but are typically used in situ as intermediates for the preparation of other 2-substituted carbapenems. For example, Scheme B illustrates a general method used to prepare the amidine carboxylate esters of Formula V and the corresponding amidine carboxylic acids of Formula VI.

SCHEME B

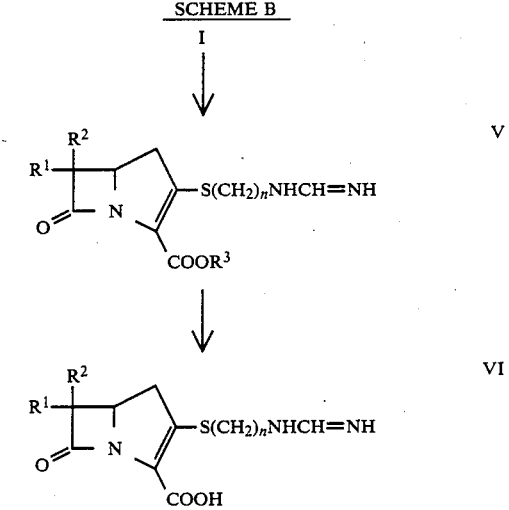

Example 3, Step C, illustrates the method of Scheme B as applied to the preparation of N-formamidoyl-thienamycin (that is, Formula VI in which n is 2 and one of $R^1$ and $R^2$ is hydrogen and the other of $R^1$ or $R^2$ is 1-hydroxyethyl). A variant method for preparing N-formamidoylthienamycin is described in U.S. Pat. No. 4,292,436 and by I. Shinkai et al., *Tetrahedron Lett.*, 23, 4903–4906 (1982).

Using various bis(chloro-substituted phenyl) phosphorochloridates, N-formamidoylthienamycin was prepared as aqueous solutions in about 81–83% overall yield (as determined chromatographically) from the corresponding ketone precursor of Formula II, p-nitrobenzyl (3R,5R,6S)-2-oxo-6-[(1R)-1-hydroxyethyl]carbapenem-3-carboxylate. See Table I, Example 5. As illustrated by Examples 3 and 4, the presence of up to about 20% contamination with tris(2,4-dichlorophenyl) phosphate had essentially no effect on the overall yield of N-formamidoylthienamycin. By way of contrast, unsubstituted diphenyl phosphorochloridate and bis(4-methoxyphenyl) phosphorochloridate each provided yields significantly less than 80%. See Table I.

The preferred embodiments of this invention include a process for preparing compounds of the following general structure:

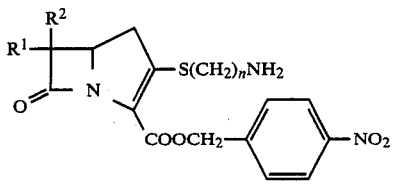

VII or a pharmaceutically acceptable acid addition salt thereof; wherein one of $R^1$ or $R^2$ is hydrogen and the other of $R^1$ and $R^2$ is 1-hydroxyethyl; comprising:

(a) reacting a mixture of a tertiary amine (preferably diisopropylethylamine) and a compound of the formula

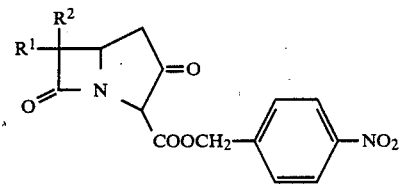

wherein $R^1$ and $R^2$ are defined as above; with a phosphorochloridate of the formula

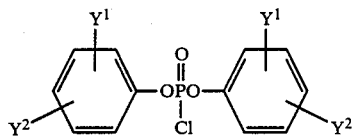

wherein $Y^1$ is chlorine and $Y^2$ is hydrogen or chlorine; in a substantially inert organic solvent (preferably N-ethylpyrrolinone) at a temperature of about $-50°$ to form an enol phosphate intermediate of the formula

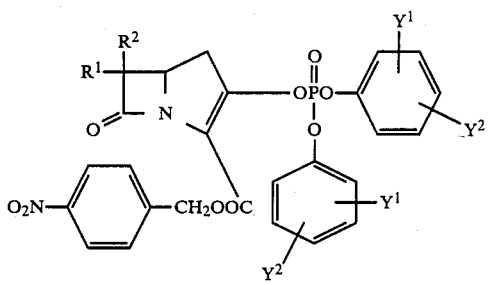

wherein $R^1$, $R^2$, $Y^1$, and $Y^2$ are defined as above; and
(b) adding to the enol phosphate intermediate cysteamine, or a pharmaceutically acceptable acid addition salt thereof (preferably the hydrochloride salt) at a temperature of from about $-70°$ to about $-60°$.

More preferred embodiments of this invention employ the following phosphorochloridates: bis(2,4-dichlorophenyl) phosphorochloridate, bis(4-chlorophenyl) phosphorochloridate, bis(3-chlorophenyl) phosphorochloridate, and bis(2-chlorophenyl) phosphorochloridate. The most preferred embodiment of this invention employs bis(2,4-dichlorophenyl) phosphorochloridate.

The following examples further illustrate details for the process of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

Yields of the various carbapenem intermediates and products were determined chromatographically using high performance liquid chromatography (HPLC) procedures readily available to those skilled in the art.

DESCRIPTION OF THE PREFERRED EMBODIMENTS

Example 1

Bis(2,4-dichlorophenyl) phosphorochloridate, Method A

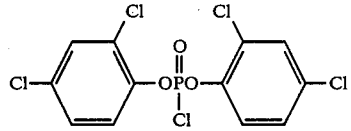

To a melt of 2,4-dichlorophenol (400.0 g, 2.454 mole) at ca. 50° was added 4-dimethylamino-pyridine (6.93 g, 56 mmole), followed by phosphorus oxychloride (289.5 g, 1.887 mole). The mixture was heated under nitrogen to ca. 120°, at which temperature the mixture began to reflux and to generate hydrogen chloride (which was passed through a sodium hydroxide scrubber). After about twelve hours at 120°-125°, gas-liquid partition chromatography (GLPC) using a silica capillary indicated less than 1% (by weight) of unreacted 2,4-dichlorophenol and a mixture of 2,4-dichlorophenyl phosphorodichloridate, the desired bis(2,4-dichlorophenyl) phosphorochloridate, and tris(2,4-dichlorophenyl) phosphate. After the reaction mixture was cooled to ca. 40°, hexane (145 ml) was added and the mixture was cooled to ca. 20°. A precipitate containing 4-dimethylaminopyridine hydrochloride was removed by filtration. The filtrate was diluted with additional hexane (145 ml) and cooled to ca. $-30°$. After about eight hours the resultant precipitate was collected by filtration and washed with hexane (four 200-ml portions) at ca. $-20°$, all with careful exclusion of moisture. Drying for two hours at room temperature under a flow of nitrogen yielded 129.87 g (26% yield) of the desired bis(2,4-dichlorophenyl) phosphorochloridate as a white solid. Analysis by GLPC indicated 99% purity (by weight), with contamination by 0.3% (by weight) 2,4-dichlorophenyl phosphorodichloridate and 0.2% (by weight) tris(2,4-dichlorophenyl) phosphate.

Example 2

Bis(2,4-dichlorophenyl) phosphorochloridate, Method B

The title compound was prepared by the general method of Example 1 with the following modifications. (1) The molar ratio of 2,4-dichlorophenol to phosphorus oxychloride was increased from 1.33 to 1.85 by using 189.99 g (1.165 mole) of 2,4-dichlorophenol and 96.60 g (0.63 mole) of phosphorus oxychloride. (2) The reaction time at 120° was increased to about 24 hours.

(3) The product was crystallized using a larger quantity of hexane (570 ml, or 3 ml per gram of starting 2,4-dichlorophenol) at −15°. Analysis by GLPC indicated 82% purity (by weight) of bis(2,4-dichlorophenyl) phosphorochloridate, with contamination by a trace of 2,4-dichlorophenyl phosphorodichloridate and 18% (by weight) of tris(2,4-dichlorophenyl) phosphate. The yield of the bis(2,4-dichlorophenyl) phosphorochloridate when corrected for purity was 125 g (53%)

Example 3

N-Formamidoylthienamycin, Method A

Step A

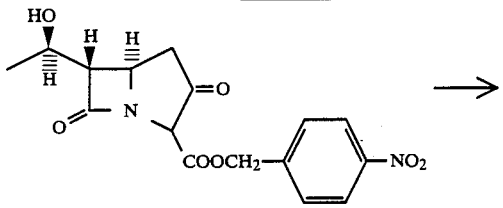

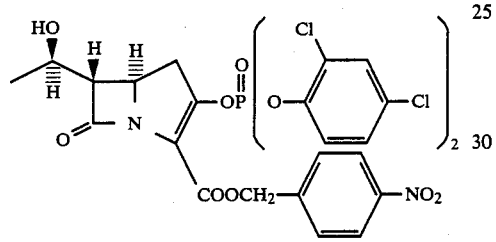

To a cooled (−50°) solution of p-nitrobenzyl (3R,5R,6S)-2-oxo-6-[(1R)-1-hydroxyethyl]carbapenem-3-carboxylate (1.964 g, 5.64 mmoles) in N-ethylpyrrolidinone (24.11 g) was added diisopropylethylamine (1.75 g, 13.5 mmoles), followed by bis(2,4-dichlorophenyl) phosphorochloridate (2.45 g, 6.03 mmole; see Example 1). The mixture was stirred for two hours and used in the next step without isolation of the enol phosphate intermediate.

Step B

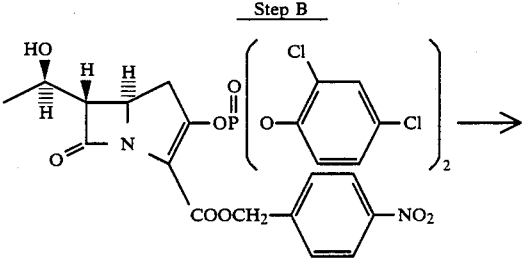

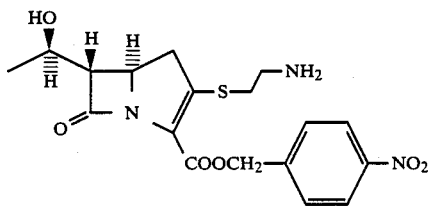

The reaction mixture from Step A was cooled to −62°. A solution of cysteamine hydrochloride (0.70 g, 6.16 mmoles) in N-ethylpyrrolidinone (2 ml) was added over a five-minute period, during which time the temperature was maintained below −60°. The reaction was stirred at −60° for 1.5 hours and used in the next step without isolation of the aminoethylthio intermediate.

Step C

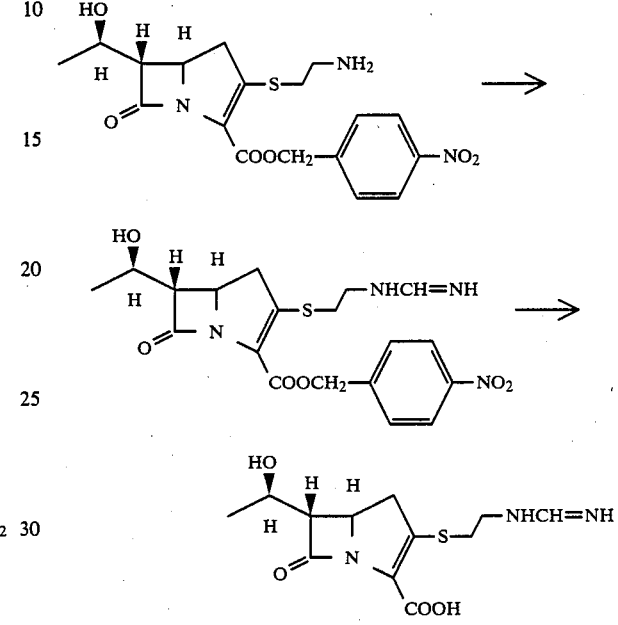

Amidine formation and hydrogenolysis of the ester group were performed using the general method described in U.S. Pat. No. 4,292,436, modified as described herein, to give the title compound in 82% yield (as determined by HPLC) in aqueous solution. A reaction mixture prepared as in Step B was maintained at a temperature of about −50°. Diisopropylethylamine (1.06 g, 8.21 mmole) was added, followed by benzyl formimidate (1.09 g, 6.35 mmole). The mixture was stirred vigorously for 20 minutes at −50°, after which HPLC indicated residual unreacted aminoethylthio intermediate. Additional benzyl formimidate (0.05 g) was added and the mixture was warmed to −20° over a fifteen-minute period and held at −20° for 20 minutes. The reaction mixture was poured into a mixture of water (150 ml), butanol (120 ml), ethyl acetate (60 ml), and 0.5M N-methylmorpholine (60 ml) at 5° and pH 6.8. Hydrogenolysis of the mixture was performed in an unthermostatted autoclave at 15° (initial) to 23° (final) using hydrogen gas (100 psi) over 20% Pd(OH)2 on carbon (0.9 g) for 1.5 hours. The mixture was filtered at 5° through a filter aid. The aqueous layer was separated and assayed for n-formamidoylthienamycin.

Example 4

N-Formamidoylthienamycin, Method B

The title compound was prepared according to the method of Example 3 except that ca. 81% pure bis(2,4-dichlorophenyl) phosphorochloridate, prepared as described in Example 2, was used. That is, 3.04 g of the phosphorochloridate-phosphate mixture (containing ca. 2.46 g of the phosphorochloridate) was allowed to react with 1.80 g of p-nitrobenzyl (3R,5R,6S)-2-oxo-6-[(1R)-

1-hydroxyethyl]carbapenem-3-carboxylate. Subsequent reaction with cysteamine hydrochloride, amidine formation, and hydrogenolysis of the ester group yielded the title compound in 82% yield (as determined by HPLC) in aqueous solution.

Example 5

N-Formamidoylthienamycin was prepared by the method of Example 3 using other substituted diphenyl phosphorochloridates. Table I lists yields, as measured by HPLC, for each phosphorochloridate.

TABLE I

N—Formamidoylthienamycin Yields from p-Nitrobenzyl (3R,5R,6S)-2-Oxo-6-[(1R)-1-hydroxyethyl]carbapenem-3-carboxylate Using Substituted Diphenyl Phosphorochloridates

| Phenyl substituent | Number of experiments | % Yield (aqueous) |
|---|---|---|
| H | 16 | 76.7 ± 0.9 |
| 2,4-Cl$_2$ | 7 | 83.1 ± 1.1 |
| 4-Cl | 11 | 82.1 ± 1.0 |
| 3-Cl | 1 | 83 |
| 2-Cl | 2 | 81 |
| 4-CH$_3$O | 1 | 73 |

What is claimed is:

1. A process for preparing a compound of the formula

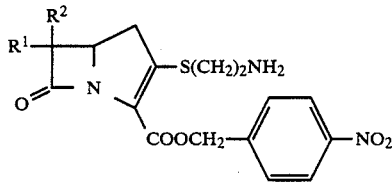

or a pharmaceutically acceptable acid addition salt thereof;
wherein one of R$^1$ or R$^2$ is hydrogen and the other of R$^1$ or R$^2$ is 1-hydroxyethyl; comprising:
(a) reacting a mixture of diisopropylethylamine and a compound of the formula

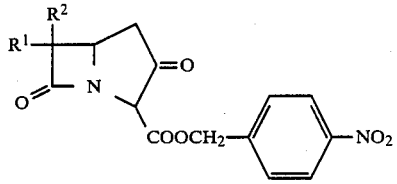

wherein R$^1$ and R$^2$ are defined as above; with a phosphorochloridate of the formula

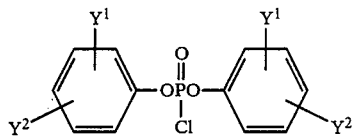

wherein Y$^1$ is 4-chloro, Y$^2$ is hydrogen or 2-chloro; in N-ethylpyrrolidinone at a temperature of about −50° to form an enol phosphate intermediate of the formula

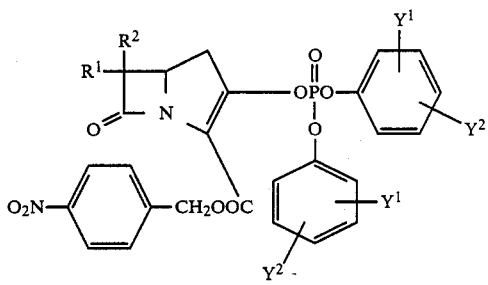

wherein R$^1$, R$^2$, Y$^1$, and Y$^2$ are defined as above; and
(b) adding to the enol phosphate intermediate cysteamine hydrochloride at a temperature of from about −70° to about −60°.

2. A process according to claim 1 wherein the phosphorochloridate is bis(2,4-dichlorophenyl) phosphorochloridate.

3. A process according to claim 1 wherein the phosphorochloridate is bis(4-chlorophenyl) phosphorochloridate.

* * * * *